United States Patent [19]
Howard, III

[11] Patent Number: 5,945,341
[45] Date of Patent: Aug. 31, 1999

[54] SYSTEM FOR THE OPTICAL IDENTIFICATION OF CODING ON A DIAGNOSTIC TEST STRIP

[75] Inventor: Willis E. Howard, III, Elkhart, Ind.

[73] Assignee: Bayer Corporation, Elkhart, Ind.

[21] Appl. No.: 08/734,103

[22] Filed: Oct. 21, 1996

[51] Int. Cl.$^6$ ............... G01N 33/48; G01N 33/52; G01N 33/50
[52] U.S. Cl. ................. 436/46; 436/50; 422/58
[58] Field of Search ............ 436/46, 50; 422/58

[56] References Cited

U.S. PATENT DOCUMENTS

| | | | |
|---|---|---|---|
| 4,592,893 | 6/1986 | Poppe et al. | 422/56 |
| 5,477,326 | 12/1995 | Dosmann | 356/406 |
| 5,597,532 | 1/1997 | Connolly | 422/58 |

FOREIGN PATENT DOCUMENTS 9607907  3/1996  WIPO.

Primary Examiner—Elizabeth Kemmerer
Assistant Examiner—David S. Romeo
Attorney, Agent, or Firm—Jerome L. Jeffers

[57] ABSTRACT

Disclosed is an automated method for reading a test strip for the analysis of one or more analyte in a liquid test sample. The method involves the spectrophotometric reading of a test strip which bears at least two marker fields on its surface which are capable of reflecting light at different spectral regions from each other. The reading means of the spectrophotometer is programmed to discern information concerning the strip, such as what analyte the strip is designed to detect, from the sequences of spectral classifications by spectral reflectancy measurements of the strip's marker fields.

21 Claims, 7 Drawing Sheets

SYSTEM FOR THE OPTICAL IDENTIFICATION OF CODING ON A DIAGNOSTIC TEST STRIP

BACKGROUND OF THE INVENTION

The present invention is concerned with diagnostic test strips and a method for their optical identification.

Test strips for the analysis of components in a liquid such as a human body fluid are well known. Typically, such strips are made of an absorbent material in which there is absorbed a reagent system which responds to the presence of a pre-selected analyte in the test fluid with a visually detectable signal such as a change in color. This change in color, which appears in one or more test field of the strip, can be the result of an enzymatic reaction in which a redox dye is oxidized or reduced to produce the colored response. Alternatively, the strip is made of a material through which the analyte and labeled antibodies specific therefor can flow to form analyte/labeled antibody conjugates which are captured in a specific detection zone of the strip to provide a detectable response when analyte is present in the fluid sample. These devices can employ either a sandwich type format in which the response is directly proportional to the concentration of the analyte in the test fluid or a competitive format where the intensity of the response is inversely proportional to the analyte concentration. While the detectable response obtained using such strips can be observed visually to obtain a qualitative or semiquantitative measure of the analyte in the test sample, greater quantitation and faster, more reliable handling of multiple test strips can be realized by reading the developed test strips instrumentally, typically by the use of a reflectance spectrometer which determines the intensity of reflection from the test field surface. This sort of instrument determines the intensity of the reflected light in the developed strip by illuminating the strip with light at one angle (typically 90°), detecting the reflected light at a different angle (typically 45°) and selecting the measured color or wavelength range at either the source or detector. The signal at the detector is typically amplified, converted to digital form and analyzed by computer. Conventionally, at the beginning of the test, the operator of the device will input information via a keyboard or other means to tell the instrument what analyte the particular strip is designed to test, so that the read out may be correlated with an appropriate reference. Thus, if the test were designed to determine the presence of hCG in the test sample, the read out would be correlated with a reference value corresponding to the presence of hCG. Because of the need for operator input, the degree of automation of the operation is less than complete and various techniques have been developed to further automate the process by providing the strips with indicators from which the device can determine the analyte to which a particular test strip is directed without the need for operator intervention.

An example of such an automated system is described in U.S. Pat. No. 5,439,826. This disclosure involves a microstrip containing a series of wells for ELISA assays in which the individual wells contain a physical characteristic, such as reflectance, in a predetermined order. The instrument detects the presence or absence of the physical characteristic and interprets this as a binary response which correlates with the particular analyte.

In U.S. Pat. No. 4,592,893 there is disclosed an analysis test strip having a test field and a separate bar code for storing batch specific information necessary for the quantitative evaluation of the reaction carried out on the test field. The bar code consists of individual code bars of differing width running substantially transversely to the longitudinal dimension of the test strip. The code bars are of narrow and broad width and the batch specific information is designed to be interpreted by a reading device in which a narrow bar represents a logical 0 and a wide bar represents a logical 1 with the distances between the code bars providing similar information. The strip reading device is programmed to interpret the logical 0 and 1 responses as a binary code corresponding to the batch specific information imputted to the test strip.

U.S. Pat. No. 5,126,952 discloses a method of providing data in bar code form useful for the determination of the calibration curve of a lot of test elements in a chemical analyzer wherein the curve corresponds to the mathematical formula:

$$C = a_0 - a_1 \cdot R - a_2 \cdot (R)^K$$

where C is the predicted concentration of the fluid test sample being analyzed, R is the response actually measured in the analyzer, K is a coefficient assigned to the analyzer and $a_0$, $a_1$ and $a_2$ are calibration coefficients. It is stated that solving this equation as described in the patent is advantageous in that a single bar code strip of only a few digits can be accurately provided with the data needed to pass on a calibration code for a given lot of test elements to the user.

SUMMARY OF THE INVENTION

The present invention is an automated method for the reading of a test strip for the analysis of an analyte in a liquid test sample. The method comprises the steps of:

a) providing a test strip having at least one test field and at least two distinct marker fields on its surface which marker fields reflect light at specific ranges of wavelengths which differ from each other in a coded sequence of spectral regions which coded sequence correlates to information concerning the test strip;

b) introducing the test strip into a strip reading device equipped with reading means for the fields which reading means comprises a light source as transmitter and a light sensitive element as receiver, which receiver is capable of differentiating between the specific ranges of wavelengths at which the marker and test fields reflect, which strip reading device is also equipped with means for correlating the spectral reflectance value at each specific spectral region of reflected light with preprogrammed information concerning the test strip. The correlating means is in operative communication with the receiving means. The strip reading device has means for moving the strip and the receiving means relative to each other, so that the reflectances of the test field and marker fields can be individually read by the reading means;

c) allowing the spectral reflectance values at the various wavelength ranges reflected by the test and marker fields to be individually read by the reading means; and d) allowing the reading means to communicate the sequence of spectral reflectance values measured from the marker fields to the correlating means and allowing the correlating means to correlate the sequence of spectral reflectance values with the preprogrammed information concerning the test strip.

The spectral reflectance values are read by the reading means by either moving the strip and reading means relative to each other or by providing a reading means which is capable of acquiring spatial and wavelength reflectances across the length of the strip, such as by illumination with various light emitting devices and detecting with an array of detectors.

DESCRIPTION OF THE INVENTION

Figure 1:
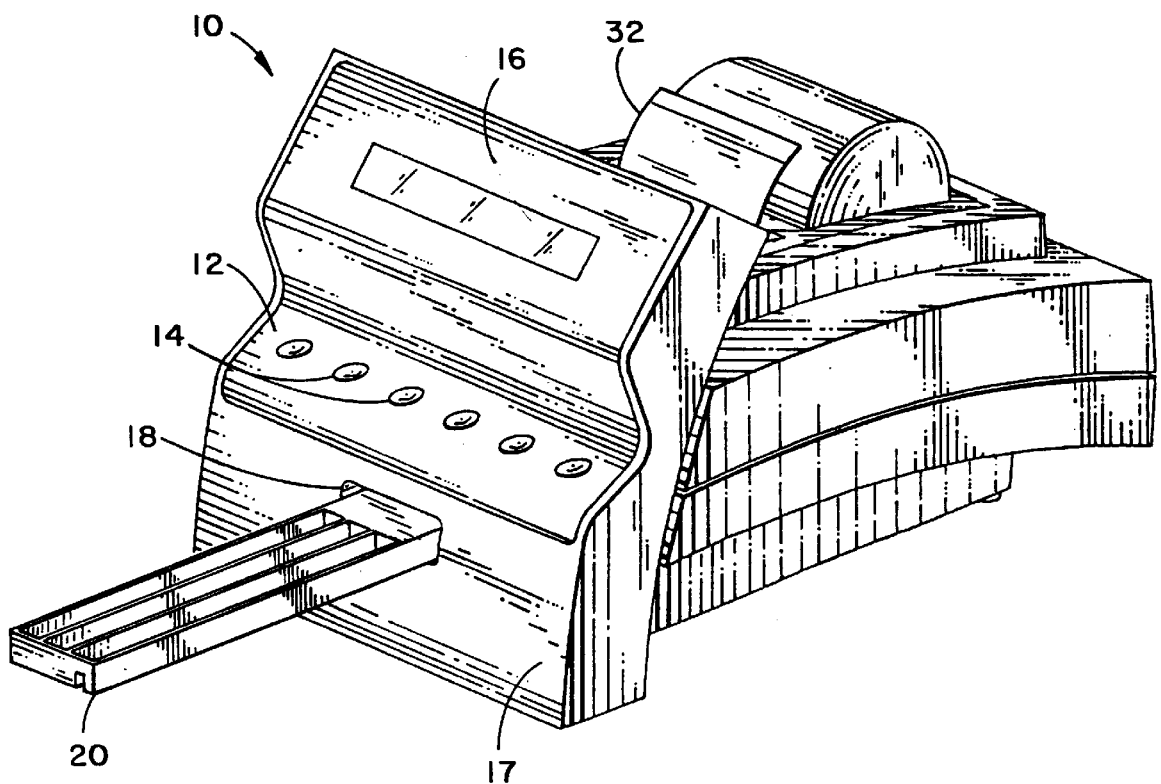
FIG. 1 is a perspective view of a reflectance spectrometer which may be used to read the test strip as called for by the present claims.
Figure 2:
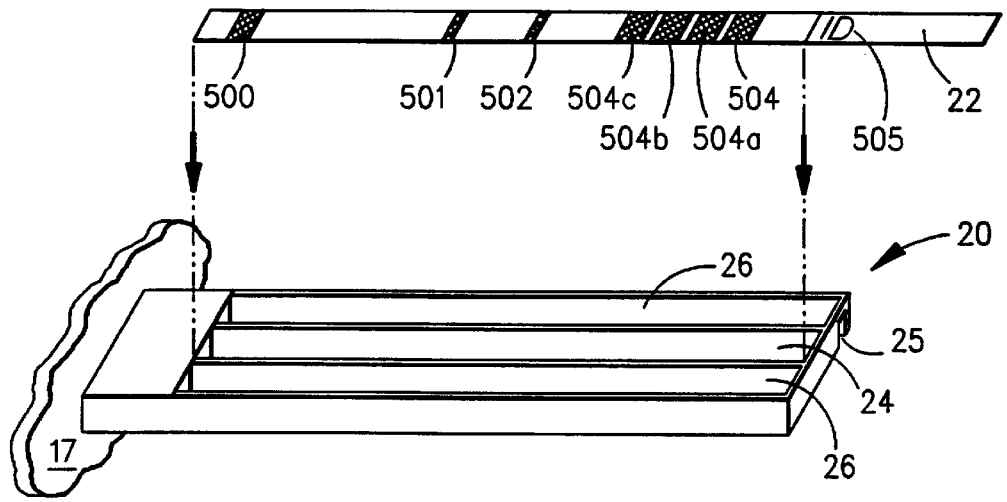
FIG. 2 is a perspective view of a test strip and a reagent strip tray used with the spectrometer of FIG. 1.

FIG. 1 illustrates a reflectance spectrometer for performing various tests, such as urinalysis tests, on a test strip such as a reagent chemistry or immunochemistry strip. The spectrometer 10 has an integral keyboard 12 with a number of entry keys 14 that may be depressed by the user. A visual display 16 for displaying various messages relating to operation of the spectrometer 10 is disposed above the keyboard 12. Referring to FIGS. 1 and 2, the spectrometer 10 has a front face 17 and an opening 18 therein in which tray 20 for carrying a test strip 22 is retractably disposed. The tray 20 has a central channel 24 and two side channels 26 formed therein. The central channel 24 is sized to conform to the shape of the test strip 22.

Referring to FIG. 2, the reagent test strip 22 has a thin, non-reactive substrate (not shown) on which are laid a number of relatively absorbant layers of material impregnated with reagents in specific locations referred to herein as test fields in which a color change, readable by the spectrometer, takes place as an indication of the presence and/or concentration of analyte in the test fluid. When the end of the strip 22 up to label 500 comes into contact with a fluid test sample such as urine, the liquid migrates up the strip, due to the absorbant nature of the strip material, to cause a color change in stripe 502 which is a control stripe that changes color if sufficient sample volume is detected.

To carry out an analysis of a liquid test sample, such as a urinalysis, the reagent strip 22 is dipped into a urine sample to be tested up to label 500 and then placed in the central channel 24 of the spectrometer tray 20. The operator presses one of the start keys 14 to initiate testing which causes the tray to be automatically retracted into the spectrometer 10. The strip may bear a visually readable identification 505 as its label. After the test strip is retracted into the spectrometer, the apparatus may need to measure some portions of the strip if very short readings are needed for any test that could be placed in the device. Then, the instrument positions the read head relative to strip 22 at the location of identification (ID) bar code 504 and determines the spectral signature by analysis of the spectral reflectance values. In one embodiment of the present invention, the color bar code 504 is white and the spectrometer is preprogrammed to read this as representing a conventional dry phase chemistry reagent strip. Another color could be used to inform the spectrometer that a different reagent system, e.g. immunochromatographic, was being read. This serves the purpose of automatically analyzing the strip in the proper way and generating a report. The instrument can be programmed to read the other marker fields; e.g. 504a, 504b and 504c, to correlate the sequence of reflected wavelengths with preprogrammed information concerning the test strip.

Figure 5:
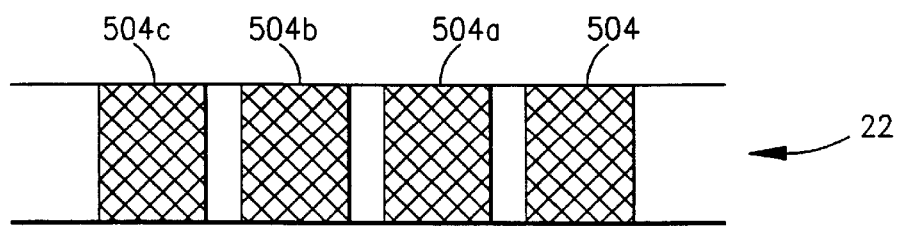
FIG. 5 is an expanded view of color coded bars on the test strip.
Figure 6:
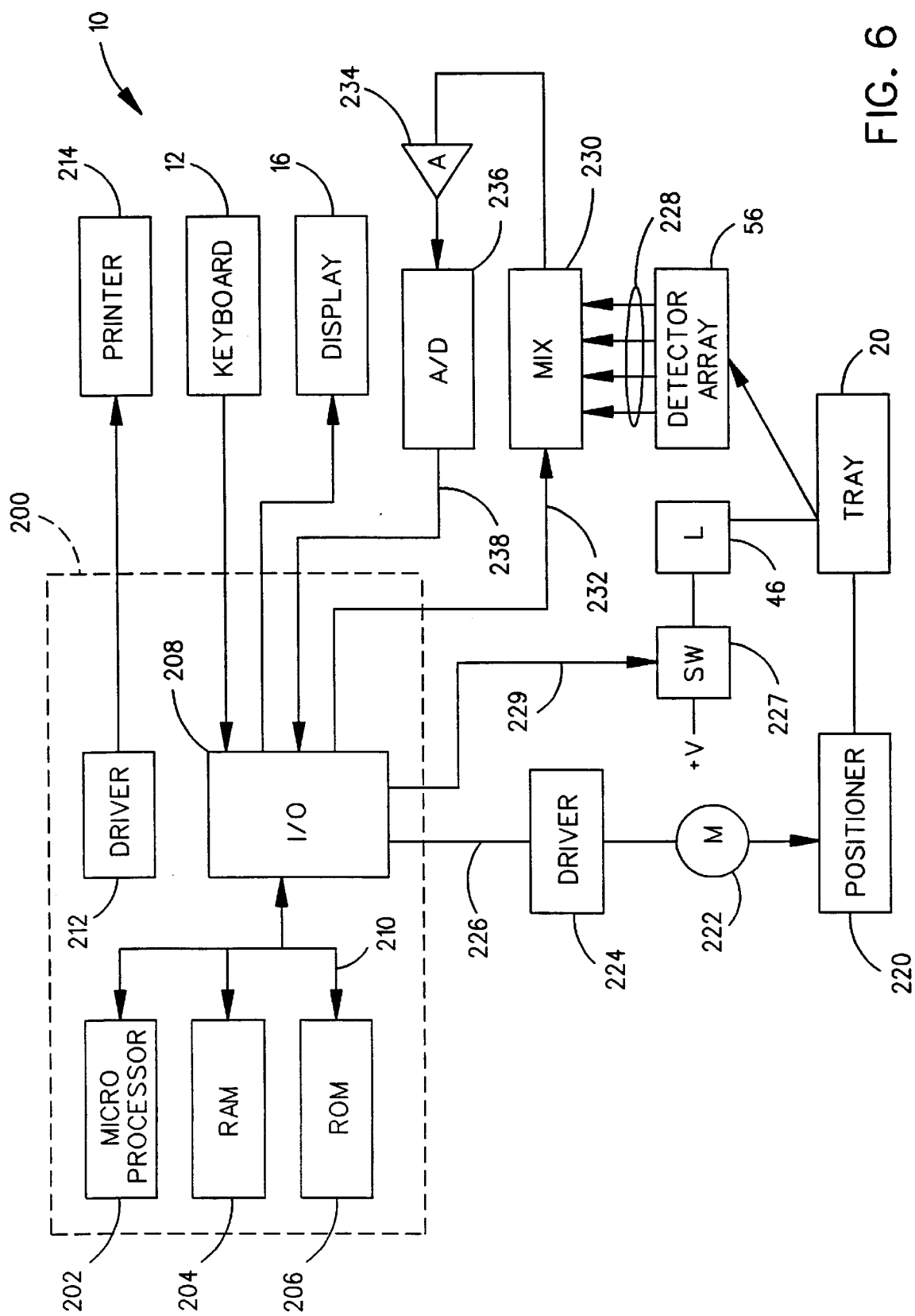
FIG. 6. is a block diagram of the electronics of the spectrometer of FIG. 1.
Figure 7:
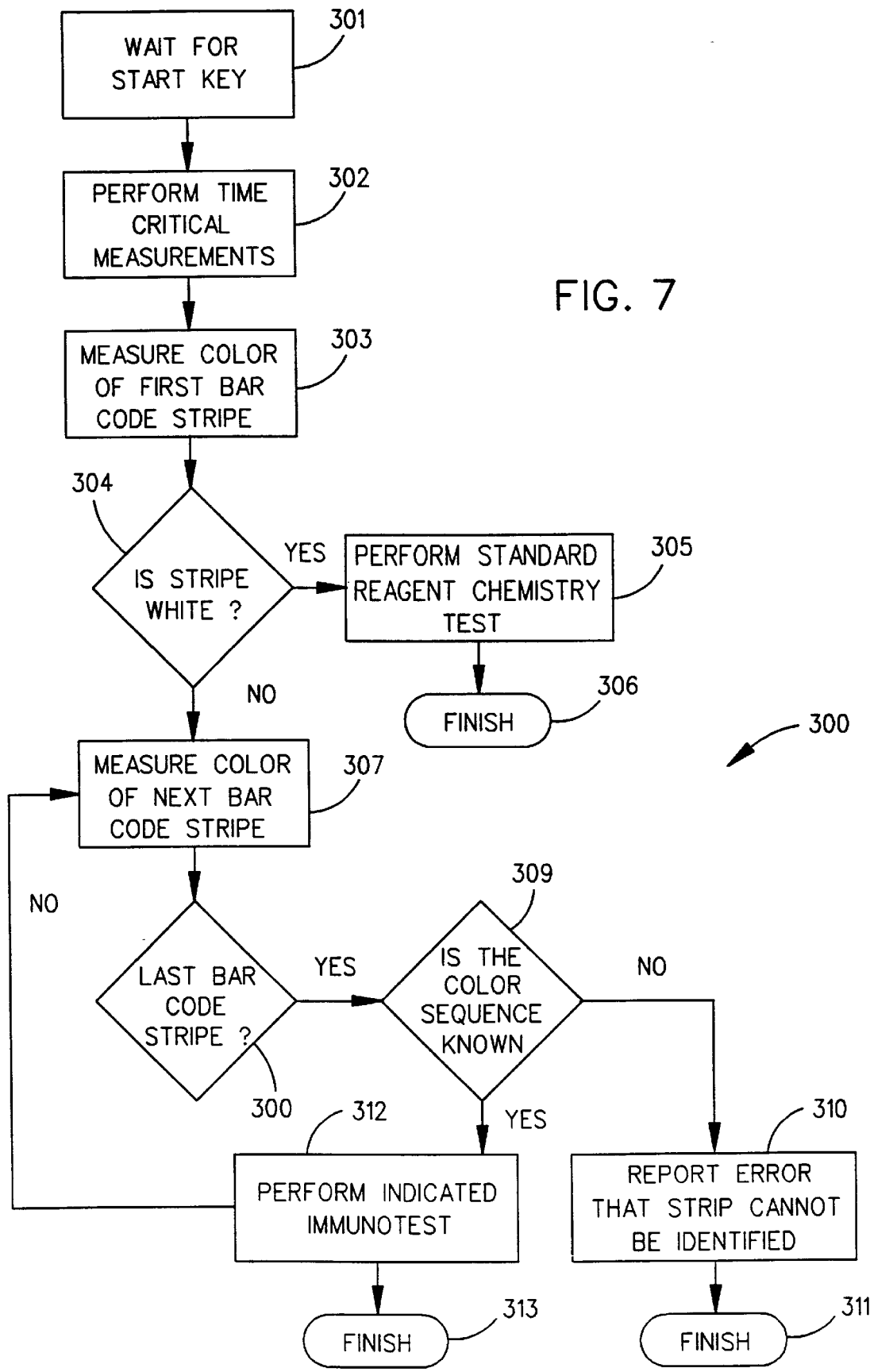
FIG. 7 is a flowchart of a computer program routine that may be used to correlate the spectral reflectance values of the color coded bars with preprogrammed information concerning the test strip. The series of bars define specific unique color sequences for the information concerning the test strip.

The operation of the spectrometer is schematically illustrated by FIG. 6. Referring to FIG. 6, the operation of the spectrometer 10 is controlled by a computer program stored in the ROM 206 and executed by the microprocessor 202. The flowchart of a routine 300 which relates to the correlation of the color coded marker fields is shown in FIG. 7. The user signals the spectroscope 10 that a test strip 22 is ready to be placed in the tray by pressing the start button 4. The microprocessor 202 waits at step 301 of FIG. 7 until this signal is detected. For some test strips there are test fields which must be read very quickly, so there is insufficient time for the marker fields to be read before taking a reading of the test field. For example in the analysis of some analytes, such as leukocytes, the chemistry reacts so quickly that if the device were to wait to take the first reading for the analyte until after reading the bar code, the reading would occur too late. Accordingly, the leukocyte position is always read first even if it turns out that the strip has no leukocyte reagent. In this event, step 302 calls for positioning the tray 20 relative to the read head 34 and takes all required reflectance measurements from the test strip beginning with the test field and followed by the reading of the marker fields. If it is later determined that measurements of the reflectance from the test fields is not required, such as in the case where the system is reading an immunotest strip, these measurements can be discarded. At step 303 the spectrometer 10 positions the tray 20 relative to the readhead 34 at the first marker field 504 which, in FIG. 5, can be depicted as reflecting blue wavelengths. The amount of light sensed by the detectors is proportional to the amount of light reflected from the color bar (marker field) at the various wavelengths. For example, if the amount of reflected light is above 85% in the red and in the green and in the blue, the spectrometer would determine the color of the marker field to be white. The color coding system of the present invention can be used to communicate information concerning tests that can be performed by traditional dry chemical reagents strips or immunochromatographic strips. Thus, in a preferred embodiment of the present invention, the spectrometer is programmed to recognize that a traditional dry chemical reagent strip is being viewed when marker field 504 is white. In this case, at step 304 the software will branch to step 305 and perform a standard chemistry test reading such as that which can be carried out using a Multistix® 10 SG reagent test strip from Bayer Corporation. At step 304, if the spectrometer determines that the color of the first bar 504 is not white, but some other color such as blue, green, black or red, then at step 307 the spectrometer will position the tray relative to the readhead at the next bar 504a and measure its color. At step 308, the spectrometer determines that there are more color bars to read by reaching the maximum number of bars or recognizing a specific short sequence as the bars are read. For example, if the bar is white, there is only one bar in the sequence. The software loops to step 307 and positions the tray relative to the readhead at the next colored bar and measures its color. This step is repeated for each of the colored bars on the strip. At step 308, if the spectrometer determines that there are no more color coding bars to read, the software loops to step 309.

At step 309, if the spectrometer determines that the color sequence does not correspond to any known test strip, the software branches to step 310 and reports an error. If the color sequence does correspond to a known test strip as correlated with the preprogrammed information at step 309, the software branches to step 312 and performs the indicated test.

The following is a detailed description of how the method of the present invention would decode the reflectances of the colored marker fields on the test strip. After the instrument has positioned the tray containing the test strip under the read head at the position of one of the marker fields, e.g. bars of a color coded bar code, the reflectance of the marker field is measured at each color (i.e. spectral region) that can be detected by the instrument. For example the Cliniteke® 50 reflectance spectrometer would measure reflectance in the blue, green, red and infrared regions of the spectrum. The infrared region is not a color, but is instead a well defined spectral region.

Figure 8:
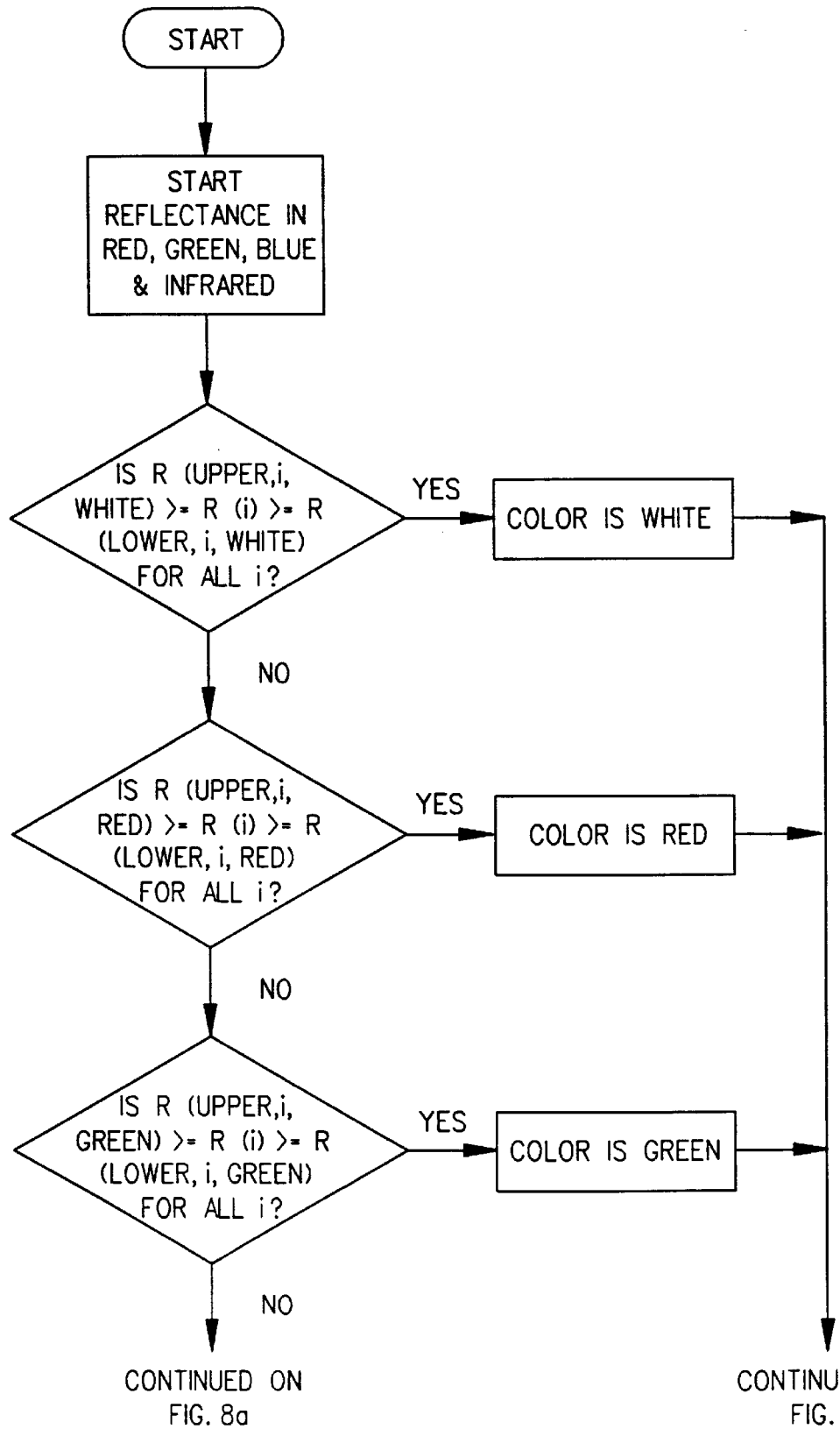
FIG. 8 (continued on FIG. 8A) is a flowchart of a computer program to analyze the color or spectral classification of a specific identification bar.
Figure 8A:
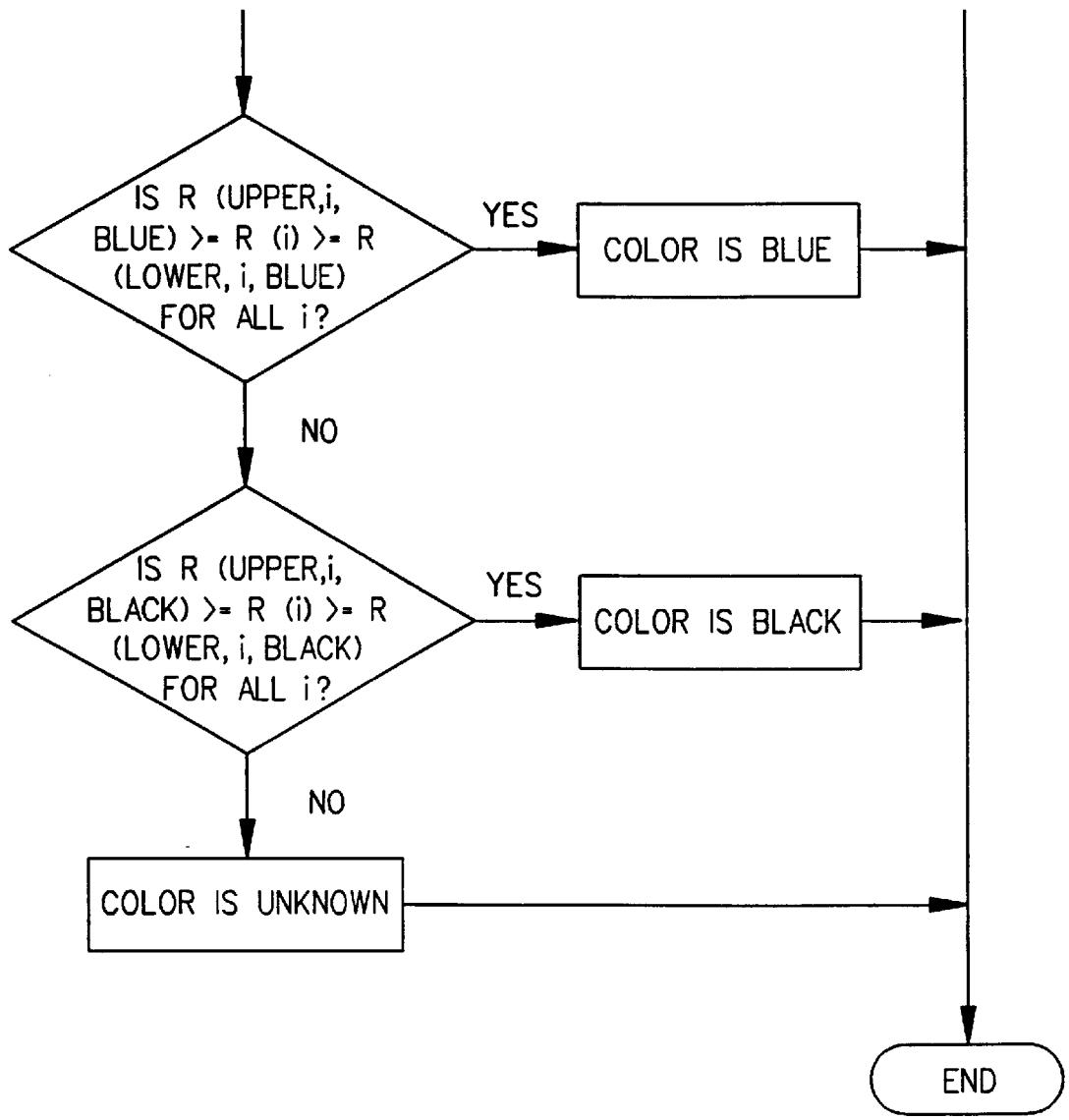

By design, the marker fields on the test strip will be limited to a finite number of colors or classifications based on the measurable reflectances. For example, a stripe or bar could be classified as only red, green, blue, black or white. For each possible classification, there will be a unique set of ranges of instrumentally measurable reflectances for the instrumentally measurable colors or spectral regions. For example, if $R_{detector}$ is the measured reflectance of a marker field for the detection of a specific colored wavelength, $R_{upper,\ detector,\ classification}$ is the upper limit for the detection of a specific color or spectral region to meet a specific classification, and $R_{lower,\ detector,\ classification}$ is the lower limit for the detection of a specific color or spectral region to meet a specific classification, then, in general, a classification is met when: $R_{upper,\ detector,\ classification} \geq R_{detector} \geq R_{lower,\ detector,\ classification}$ and is true for all detected spectral regions. The upper and lower limits will generally be different for each different color of stripe or bar used as the marker field. The classification process is summarized in the flow chart of FIG. 8. More specifically, FIG. 8 represents the means of conversion of measured spectral reflectance values to named spectral classifications.

For example, a marker field may be classified as white if all of the following conditions are met:

100% $R \geq R_{blue} \geq 85\%$ R and
100% $R \geq R_{green} \geq 85\%$ R and
100% $R \geq R_{red} \geq 85\%$ R and
100% $R \geq R_{infrared} \geq 0\%$ R blue if the following conditions are met:

100% $R \geq R_{blue} \geq 50\%$ R and
30% $R \geq R_{green} \geq 20\%$ R and
20% $R \geq R_{red} \geq 10\%$ R and
100% $R \geq i_{nfrared} \geq 0\%$ R green if the following conditions are met:

20% $R \geq R_{blue} \geq 5\%$ R and
100% $R \geq R_{green} \geq 30\%$ R and
15% $R \geq R_{red} \geq 5\%$ R and
100% $R \geq R_{infrared} \geq 0\%$ R red if the following conditions are met:

25% $R \geq R_{blue} \geq 10\%$ R and
15% $R \geq R_{green} \geq 5\%$ R and
100% $R \geq R_{red} \geq 50\%$ R and
100% $R \geq R_{infrared} \geq 0\%$ R and black if the following conditions are met:

15% $R \geq R_{blue} \geq 0\%$ R and
15% $R \geq R_{green} \geq 0\%$ R and
15% $R \geq R_{red} 0\%$ R and
100% $R \geq R_{infrared} \geq 0\%$ R It can be seen from this example that these conditions are mutually exclusive and that a marker field can be classified into one classification at most. If a stripe cannot be classified into one of these classifications, then an unrecognized or unknown color must result in the report of an error on the part of the instrument. These ranges will properly describe one set of colors that are specifically formulated through the pigment selection to have certain shades of white, red, green, blue and black. Other shades of white, red, green, blue and black will have other limits and the use of other colors will result in still other limits. Selection of the limits for different shades of colors or spectral regions will be apparent to those skilled in this art in view of the foregoing description. Once the spectrometer has read the color code, this code can be correlated with a preprogrammed code by the software, as previously described, which then instructs the device concerning the coded information about the strip. For example, if the strip is designed for the detection of calcium in urine, the device, upon being appraised of this fact, will measure the specific reflections at the specific times and locations on the strip for that test, analyze the data and generate a report.

A close up drawing of four color bar codes is shown in FIG. 5. In a preferred embodiment, the width of the colored bars is 0.150 inch and the separation between bars is 0.050 inch. Also in a preferred embodiment the colors red, green, blue, black and white are the possible colors of the bar codes. Alternatively, the colors could be red, green, black and white; other color selections are, of course, suitable provided that the spectrometer is provided with a suitable detection system. The selection of the spectral regions for the marker fields need not be limited to the visible region of the spectrum since the spectrometer can be equipped to detect radiation in the infrared or other non-visible regions.

The color coding sequence of the present invention can provide information not only about the particular analyte to which the strip is sensitive, but can also allow the software to look up information on critical measurement parameters such as location of reacting areas, critical times, strip age, and reactivity. After the color sequence has been identified, the instrument will move the test strip 22 to the proper location, i.e. test field 501 and collect data at the proper wavelengths and at the proper time or times such that the collected data can be analyzed by an appropriate algorithm to complete the assay. These data are collected by illuminating the test field 501 with white light from the light source and determining the amount of reflectance from the test field based on the detection of light received from the illuminated portion of the strip 501 at an angle (e.g. 45 degrees) from the upper surface of the strip 22. In another embodiment, the sample could be illuminated with colored light and the detector could detect all wavelengths.

The present invention is further illustrated by the following examples in which CLINITEK® spectrophotometers were used. The CLINITEKO® 50 and CLINITEK® 500 instruments have the ability to read diffuse reflectance in the blue, green, red and IR spectral regions. The instruments also have the ability to position any relevant region of the strip relative to the optical system, thus measuring the reflectance values for each of the four ID band positions in the blue, green, red and IR regions. These reflectance values are referred to herein as spectral intensities or spectral diffuse reflectance values because they are the reflectance values as a function of wavelength. In this case, intensity refers to the magnitude of the diffuse reflectance signal. The set of four spectral diffuse reflectance values at each ID band position is compared by the instrument with predetermined limits to identify the color of each ID band position. After the four ID band position colors have been determined, the ordered set of colors is compared to a table of known color strip color ID sequences. For example, if the band sequence evaluates to "Blue Black White White" then the test is identified as being directed to hCG. If the band sequence does not correspond to any known strip, an error condition results.

Another term for describing the ordered set of ID band colors is spectral signature where the color is determined by analysis of the four spectral diffuse reflectance values. Spectral intensity or spectral diffuse reflectance value is another way of describing the diffuse reflectance value for any one spectral range (e.g. IR from 825 nm to 855 nm at any location such as the first ID band).

In actual operation, the user may for example want to analyze an immunoformat test strip 22 FIG. 2 for a particular substance. The user dips the strip into a sample of urine up to the indicated level 500 for a predetermined time such as 30 seconds. The strip is then immediately withdrawn from the sample. While the strip is being withdrawn, the start key 12 of the instrument 10 FIG. 1 is pressed. The strip is placed on the table 20 FIG. 2 within 10 seconds.

Figure 3:
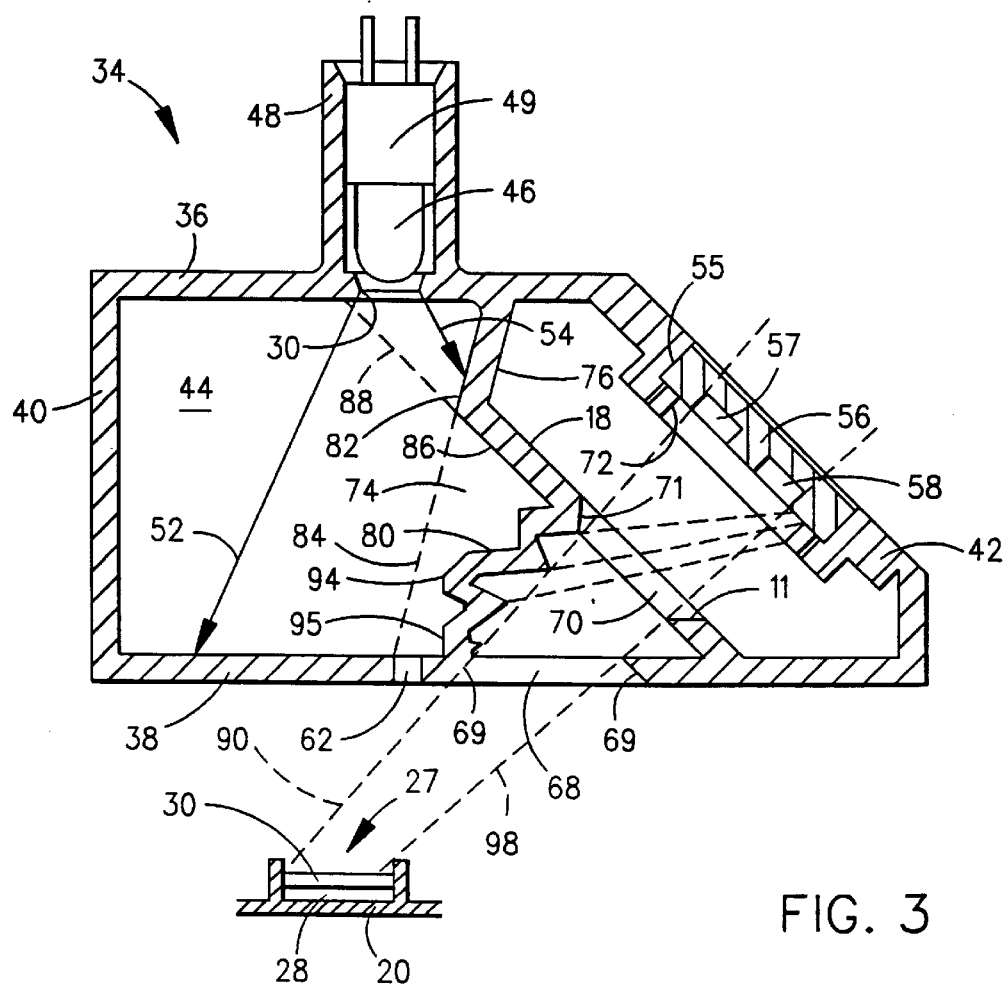
FIG. 3 is a cross-sectional view of a read head suitable for use with the spectrometer

The instrument homes the table, measures the reflectance of the calibration chip on the table 20 FIG. 2 and positions the reagent pad under the read head 34 FIG. 3 as determined by the selected type of multiple reagent test strip. An initial read of the reagent pad is made at an initial time in case it is determined by reading the color coded marker sequence that a multiple reagent test strip has been placed in the instrument. This is done because reading the initial reflectance value of the pad after reading a marker field will delay reading the pad beyond the time required for the initial reading of the pad. In this example, a strip with a pad designed for detecting leucocytes is used. If it is later determined that there is no leukocyte pad, this initial reading is discarded.

The instrument 10 FIG. 1 proceeds to position the test strip 22 FIG. 2 with marker field 504 under the read head 34 FIG. 3. The diffuse reflectance of the marker field 504 FIG. 2 is measured in the infrared (IR), red, green, and blue spectral regions. If, for example, all 4 spectral diffuse reflectance values exceed 85 percent reflectance then marker field 504 FIG. 2 is classified as white. A classification of marker field 504 FIG. 2 as white is the indication that the selected type of multiple reagent test strip has been placed on the table 20 FIG. 2 of instrument 20 FIG. 1. In this case, a standard urinalysis of the selected type of multiple reagent test strip is performed at the read times and with the algorithms known by the instrument 10 FIG. 1 to apply to the test strip. If any of the 4 spectral diffuse values does not exceed 85 percent reflectance then marker field 504 FIG. 2 is not classified as white, but will be classified as another color based on the set of spectral diffuse reflectance values. If, for example, the diffuse reflectance value in the blue exceeds 50 percent reflectance and the diffuse reflectance value in the green is between 20 and 30 percent reflectance and the diffuse reflectance value in the red is between 10 and 20 percent reflectance then marker field 504 FIG. 2 is classified as blue.

In this example, the diffuse reflectance in the infrared spectral region is not used as part of the classification. For some pigments that are placed in a marker field, the infrared can be used as part of the classification. When the infrared is used as part of the classification, standard names of colors may not apply to the classification since the classification would be based on reflectance in spectral regions that are not visible and thus play no role in the perception and classification of colors.

After classification of the marker field 504 FIG. 2, the instrument 10 FIG. 1 positions the table 20 FIG. 2 with marker field 504*a* under the read head 34 FIG. 3. The diffuse reflectance of the marker field 504*a* FIG. 2 is measured in the infrared (IR), red, green, and blue spectral regions. For example, if the spectral diffuse reflectance values in the red and in the green and in the blue spectral regions are all less than 15 percent reflectance then the marker field 504*a* FIG. 2 is classified as black. After classification of the marker field 504*a* FIG. 2 the instrument 10 FIG. 1 positions the table 20 FIG. 2 with marker field 504*b* under the read head 34 FIG. 3. The diffuse reflectance of the marker field 504*b* FIG. 2 is measured in the infrared (IR), red, green, and blue spectral regions. If, for example, all 4 spectral diffuse reflectance values exceed 85 percent reflectance, then marker field 504*b* FIG. 2 is classified as white. After classification of the marker field 504*b* FIG. 2 the instrument 10 FIG. 1 positions the table 20 FIG. 2 with marker field 504*c* under the read head 34 FIG. 3. The diffuse reflectance of the marker field 504*c* FIG. 2 is measured in the infrared (IR), red, green, and blue spectral regions. If, for example, all 4 spectral diffuse reflectance values exceed 85 percent reflectance then marker field 504*c* FIG. 2 is classified as white.

In this example, a classification sequence of (blue, black, white, white) was determined for marker fields (504, 504*a*, 504*b*, 504*c*) of strip 20 FIG. 2. If this classification sequence is not known to the instrument 10 FIG. 1 then an error message will be shown on instrument display 16 FIG. 1. If this classification sequence is known to the instrument 10 FIG. 1 as an indication of a particular immunotest then the analysis of the immunotest bands will proceed. For this example, (blue, black, white, white) could indicate an hCG test with one test control region 502 FIG. 2 and one test region 501.

The instrument 10 FIG. 1 will position the test control region 502 FIG. 2 under read head 34 FIG. 3 and measure the diffuse reflectance in the infrared (IR), red, green, and blue spectral regions. The time dependent diffuse spectral reflectance measurements are analized in a way that is specific to the test identified by classification sequence (blue, black, white, white). The analysis of the test control region will indicate whether or not the proper procedural methods were followed. For example, the reflectance in the red may be computed and then compared with a table of reflectance ranges to determine if the proper procedural methods were followed. Analysis of the test control region will either allow the test results to be analyzed or result in an error message on display 16 FIG. 1 indicating that the proper procedural methods were not followed. The test region 501 FIG. 2 is measured in the infrared (IR), red, green, and blue spectral regions. Measurements may be taken at different times and may be taken at different positions. The time dependent diffuse spectral reflectance measurements are analyzed in a way that is specific to the test identified by classification sequence (blue, black, white, white). For example, the ratio of the reflectance in the green to the reflectance in the infrared may be computed and then compared with a table of ratio ranges to decode the concentration of the substance that will be reported to the user. If there was no error, the analysis results may be reported on printer 32 FIG. 1.

In another preferred embodiment, there is also a control region 502 that will generate a specific color if the proper procedures for the test is followed by the user. More particularly, if the test strip were not exposed to sufficient sample, this procedural fault will be detected.

The steps of transmitting the light to the test strip (both the test field and the marker fields) and detecting the wavelength of the reflected light are accomplished by the read head. FIG. 3 represents a preferred embodiment of a read head suitable for use in the present invention. Referring to FIG. 3, the read head 34 illuminates portions of the test strip 22 and detects light reflected from the stripes 501 and 502 or color fields 504. Also depicted is a portion of the tray 20 on which the reagent strip 22 is disposed. The read head 34 has a housing with a top wall 42, a planar back wall 44 and a planar front wall (not shown) parallel to the back wall 44. An illumination source in the form of a light bulb 46 is supported directly above the reagent stripe 201, 202 or bar 203, 204 to be tested via a cylindrical housing portion 48 integrally formed with the top wall 36. The lower spherical portion of the light bulb 46 has a concentrating lens integrally formed therein and the lower spherical surface is acid-etched to provide it with an uneven diffusing surface, so that the shape of the bulb filament does not contribute to the nonuniformity of the emitted light. When manufactured, the bulb 46 is dynamically fitted to a ceramic base 49 when the bulb is illuminated to ensure that the axial direction in which the bulb 46 emits light is substantially parallel to the longitudinal axis of the ceramic base 49. The bulb emits light through a circular aperture 50 formed in the top wall 36 to form a cone of light defined by a first edge ray 52 and a second edge ray 54.

Figure 4:
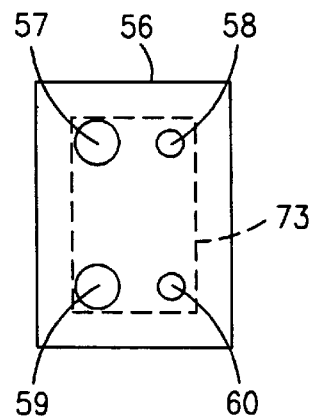
FIG. 4 is a schematic of a detector element useful in the spectrometer.

The angled side wall 42 has a rectangular aperture 55 formed therein in which a rectangular detector array 56 is disposed. The detector array 56 has four reflectance detectors 57, 58, 59 and 60, disposed therein as depicted in FIG. 4, each of which is composed of a conventional colored or infrared filter and a conventional silicon detector. Each filter allows light having a distinctive wavelength to pass through so that each of the detectors 57–60 is responsive to light of a different wavelength range. For example, the four wavelength bands of the filters could be 400–510 nm (blue); 511–586 nm (green); 587–660 nm (red) and 825–855 nm (infrared). Depending on the number of marker fields on the particular test strip being used, two or more of the detectors 57–60 may be used. Light passes through a first optical path from the light bulb 46 and through a relatively small rectangular aperture 62 formed in the bottom wall 38 to illuminate a relatively small rectangular area of the reagent stripe 502 (test field) or colored bar 504 et. seq., (marker fields) being read. The test strip 22 may be moved relative to the aperture 62, so that different rectangular areas of the test strip are illuminated.

In operation, reflected light passes through a second optical path from the illuminated area on the reagent strip 22 through a first, rectangular detection aperture 70 having angled edges 71 and through a rectangular aperture 72 formed in the angled wall 42 to a detection area 73 (FIG. 4) in which the four detectors 57–60 are disposed.

The interior of the read head 34 is provided with an irregularly shaped baffle 74 composed of a first planar wall segment 76, a second planar wall segment 78 and a zig-zag shaped wall segment 80. The shape of the baffle 74 is designed to prevent singly reflected light rays from reaching the reagent strip 22 from the light bulb 46 and to prevent singly reflected light rays from reaching the detector area 73 from the reagent pad 30.

All surfaces of the baffle 74 and all interior surfaces of the housing walls 36, 38, 40 42 and 44 are shiny, specular surfaces so that any light incident upon any surface at an angle of incidence is reflected from the surface at an angle of reflection equal to the angle of incidence. This may be accomplished by injection molding the read head 34 from a metal mold having highly polished molding surfaces. The read head 34 is preferably formed of black plastic to that only a small percentage of light, e.g. 5%, incident upon any of its internal surface is reflected. Consequently, any light that undergoes at least two reflections from any interior surfaces of the read head 34 is attenuated by at least 99.75%.

Referring to FIG. 3, the wall segment 76 has a specular surface 82 that is angled in a direction indicated by dotted line 84 which intersects the bottom wall 38 at a point just to the left of the aperture 62. Consequently, any light rays emitted by the bulb 46 that impinge upon the surface 82 are reflected to an area to the left of the aperture 62. It should be noted that any such rays are reflected at least twice before they can pass through the aperture 62. It should also be noted that no light can be reflected from the surface 82 and pass directly through the aperture 62 without further reflection since the surface 82 is not visible when the interior of the read head 34 is viewed from the aperture 62.

The wall segment 78 has a specular surface 86 angled in a direction indicated by a dotted line 88, which intersects the top wall 36 at a point to the left of the circular opening 50 through which light passes. Consequently, there is no direct path from the light bulb 46 to the surface 86. Accordingly, any light that is reflected from the surface 86 to the aperture 62 will have undergone at least two reflections from the interior surface of the read head 34.

Figure 3A:
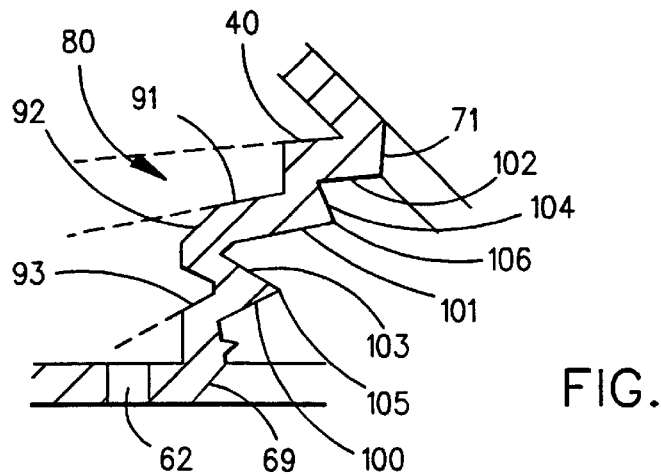
FIG. 3A is an enlarged view of a portion of the read head 34 shown in FIG. 3.

Referring to FIGS. 3 and 3A, the zig-zag wall segment 80 has angled surfaces 90–93, each of which is angled in a direction indicated by a respective dotted line. Since all of the dotted lines intersect the bottom wall 38 or the side wall 40 to the left of the aperture 62, no light that impinges upon these surfaces 90–93 directly from the light bulb 46 can be reflected directly to the aperture 62. The zig-zag wall segment 80 has two further surfaces 94, 95 (FIG. 3) that are angled so that any light that impinges on those surfaces directly from the bulb 46 is reflected exclusively to the area of the bottom wall 38 to the right side of the aperture 62.

The only surfaces from which light rays emitted by the bulb 46 can be singly reflected and still pass through the aperture 62 are the vertical walls of the aperture itself. However, such singly reflected light rays constitute an insignificant amount of the total light which passes directly from the light bulb 46 to the walls 40 or 44 to the aperture 62. However, since the bulb concentrates light in a forward direction within the cone defined by rays 52 and 54, the amount of light going through the aperture 62 from this path is insignificant.

The second optical path from the reagent strip 22 to the detector area 73 (FIG. 4) is generally indicated by a pair of dotted lines 96 and 98. The side of the zig-zag wall segment 80 which is disposed adjacent to the second optical path has a plurality of planar, specular surfaces 100, 101 and 102 which are angled in a direction indicated by a number of corresponding dotted lines (shown in FIG. 3) which intersect the angled side wall 42 at a point to the lower right of the detector area 73. Consequently, any light rays that impinge upon these surfaces 100–102 directly from the reagent strip 22 without reflection cannot reach the detector area 73 without at least one more reflection, and any such light rays will be attenuated by at least 99.75%. The wall surfaces 100 and 103 join at an edge 105 and the wall surfaces 101 and 104 join at an edge 106 with the edges 105 and 106 being substantially aligned with a respective edge of the detection area 73. The edges 69 and 71 of the detection apertures 68 and 70 are aligned with the edges of the detection area 73. In general, the instrument detects light that is transmitted through a filter having a specific wavelength range. When the range includes visible wavelengths in the range of 400 to 700 nm, a color is assigned to the filter. When the filter does not transmit any visible wavelengths, such as in the case where infrared radiation is used, the concept of color does not apply.

FIG. 6 is a block diagram of the electronics and other components of the spectrometer 10. Referring to FIG. 6, the operation of the spectrometer is controlled by a microcontroller 200 which has a microprocessor 202, a random access memory (RAM) 204, a read only memory (ROM) 206 and an input/output (I/O) circuit 208 all of which are interconnected with an address/data bus 210. The microcontroller 200, which may be a conventional microcontroller such as a DS2253T microcontroller commercially available from Dallas Semiconductor, can incorporate a driver circuit 212 connected to the I/O circuit 208 for driving a printer 214.

The microcontroller 200 controls the movement of the reagent strip tray 20 via a conventional positioner 220 mechanically coupled to the tray 20 and a motor 222 which is typically a stepping motor driven by drive signals generated by a driving circuit 224 connected to the I/O circuit 208 via an electrical line 226.

The microcontroller 200 selectively turns on the light bulb 46 via a switch 227 connected to the I/O circuit 208 via an electrical line 229. The light bulb 46 is turned on one second prior to the performance of the test so that it will be sufficiently warmed up.

Each of the detectors 57–60 of the detector array 56 may generate an electrical reflectance signal on one of a number of electrical lines 228. Each reflectance signal has a magnitude that depends on the amount of light detected by the associated detector. The microcontroller 200 can selectively read any one of the reflectance signals by transmitting a select signal to a multiplexer 230 via a line 232. The multiplexer 230 then transmits the selected reflectance signal to an amplifier 234 and an analog-to-digital (A/D) converter 236 which transmits the binary signal output by the amplifier 234 to the microcontroller 200 via a line 238 connected to the I/O circuit 208. The microcomputer analyzes the binary data from the A/D converter by processing the data through the appropriate algorithm. It then generates a report that is transmitted according to previous instructions from the operator.

I claim:

1. An automated method of reading a test strip for the analysis of one or more analyte(s) in a liquid test sample which comprises the steps of:

a) providing a test strip having at least one test field on its surface which reflects light at a specific range of wavelengths and at least two distinct marker fields on the same side of its surface as the test field which marker fields reflect light at different ranges of wavelengths from each other and from the test field in a coded sequence of ranges of wavelengths which coded sequence correlates to information concerning identification of the test strip;

b) introducing the test strip into a strip reading device equipped with reading means for both of the test and marker fields which reading means comprises a light source as transmitter and a light sensitive element as receiver which receiver is capable of differentiating between the ranges of wavelengths at which the marker and test fields reflect, which strip reading device is also equipped with means for correlating the coded range of wavelength sequence of reflected light with preprogrammed information concerning the test strip which correlating means is in operative communication with the receiving means and which reading device has means for moving the strip and receiving means relative to one another, so that the reflectance of the test field and marker fields can be individually read by the reading means;

c) allowing range of wavelength values reflected by the test and marker fields to be individually read by the reading means; and d) allowing the reading means to communicate the sequence of spectral reflectance values reflected from the marker fields to the correlating means and allowing the correlating means to correlate the sequence of reflected range of wavelength values with the preprogrammed information concerning the strip.

2. The method of claim 1 wherein the range of wavelength value reflected from the test and marker fields are read by moving the strip and reading means relative to each other.

3. The method of claim 2 wherein the strip reading device has a specimen table which is movable in relation to the reading means and wherein the strip is placed on the specimen table and moved relative to the reading means, so that the reading means can scan the marker fields.

4. The method of claim 3 wherein the strip is moved relative to the reading means a sufficient distance for the reading means to also scan the test field.

5. The method of claim 1 wherein the reading means is capable of acquiring spatial and spectral reflectances across the length of the strip.

6. The method of claim 1 wherein the information concerning the test strip is calibration information based on the particular batch from which the strip was obtained.

7. The method of claim 1 wherein the information concerning the test strip relates to which analyte or analytes the test strip is designed to analyze.

8. The method of claim 1 wherein the information concerning the test strip relates to location of reactive areas, critical times, strip age and strip reactivity.

9. The method of claim 1 in which the marker fields comprise bars which are substantially parallel to each other and are substantially perpendicular to the longitudinal axis of the strip.

10. A test strip for the analysis of one or more analytes in a fluid test sample which comprises:

a) a carrier of an absorbant material;

b) at least one test field on the surface of the carrier including at least one test field material reactive with the analyte or analytes being analyzed and capable of providing a spectrally detectable response;

c) at least two distinct marker fields on the same side of the surface of the carrier as the test field each of which marker fields having the same width as each other and being capable of reflecting light at different specific ranges of wavelengths from each other which specific ranges of wavelengths are predetermined to form a coded sequence of spectral regions which sequence correlates to information concerning identification of the test strip.

11. The strip of claim 10 wherein the absorbent material carrier is elongated.

12. The strip of claim 11 wherein the marker fields comprise bars which are substantially parallel to each other and are substantially parallel to the longitudinal axis of the strip.

13. The strip of claim 10 wherein the absorbant material is made of a material which allows the analyte and labeled antibodies specific thereto to flow through it along with the fluid test sample and to form analyte/labeled antibody conjugates which can be captured in a specific capture zone of the strip.

14. The strip of claim 10 which has four marker fields which are red, green, blue and either black or white in color.

15. The strip of claim 10 wherein at least one of the marker fields reflects in the infrared region of the spectrum.

16. The strip of claim 10 wherein the information concerning the strip to which the sequence of spectral regions correlates is the analyte for which the strip is designed to test, location of reflecting areas on the strip, critical times for reading the strip, the strip's age or the strip's reactivity.

17. The strip of claim 16 wherein the information relates to the analyte for which the strip is designed to test.

18. The strip of claim 10 wherein the information concerning the strip is calibration information which relates to the production batch from which the strip was obtained.

19. The strip of claim 10 which contains a control region which will generate a specific color if proper procedure for using the strip are followed.

20. A strip for the analysis of an analyte in urine which comprises:

a) an elongated carrier of an absorbant material which allows the analyte and labeled antibodies specific thereto to flow through it along with the urine and to form analyte/labeled antibody conjugates which can be captured in a specific capture zone of the strip;

b) a test field on the surface of the carrier which captures either the labeled antibody or the analyte/labeled antibody conjugate and is capable of providing a spectrally detectable response;

c) at least two distinct marker fields on the same side of the surface of the carrier as the test field in the form of bars which have the same width as each other and which marker fields are capable of reflecting light at a range of wavelengths different from the other which range of wavelengths are predetermined to form a coded sequence of range of wavelengths which sequence correlates to the analyte for which the strip is designed to test.

21. A test strip for the analysis of one or more analytes in a fluid test sample which comprises:

a) a carrier of an absorbant material;

b) at least one test field on the surface of the carrier including at least one test field material reactive with the analyte or analytes being analyzed and capable of providing a spectrally detectable response;

c) at least two distinct marker fields on the same side of the surface of the carrier as the test field each of which marker fields being capable of reflecting light at different specific ranges of wavelengths from each other which specific ranges of wavelengths are predetermined to form a coded sequence of ranges of wavelengths which sequence correlates to information concerning identification of the test strip and wherein at least one of the marker fields is white and which white marker field(s) correlates to the strip being a traditional dry chemistry strip.

* * * * *